United States Patent
Bodnar et al.

(10) Patent No.: US 12,168,067 B2
(45) Date of Patent: Dec. 17, 2024

(54) PHOTOSTABLE ANTIOXIDANT COSMETIC COMPOSITION

(71) Applicant: L'OREAL, Paris (FR)

(72) Inventors: Brian Scott Bodnar, Manasquan, NJ (US); Simon Pierre Donck, Saint-Ouen (FR); Jun Suzuki, Kanagawa (JP); Cherry Wang, ShangHai (CN)

(73) Assignee: L'OREAL, Paris (FR)

( * ) Notice: Subject to any disclaimer, the term of this patent is extended or adjusted under 35 U.S.C. 154(b) by 232 days.

(21) Appl. No.: 17/537,662

(22) Filed: Nov. 30, 2021

(65) Prior Publication Data

US 2022/0079863 A1   Mar. 17, 2022

Related U.S. Application Data

(62) Division of application No. 16/399,313, filed on Apr. 30, 2019, now abandoned.

(51) Int. Cl.

| | | |
|---|---|---|
| A61K 8/365 | (2006.01) | |
| A61K 8/34 | (2006.01) | |
| A61K 8/49 | (2006.01) | |
| A61K 8/60 | (2006.01) | |
| A61K 8/73 | (2006.01) | |
| A61Q 17/04 | (2006.01) | |
| A61Q 19/00 | (2006.01) | |
| A61Q 17/00 | (2006.01) | |

(52) U.S. Cl.
CPC .............. *A61K 8/602* (2013.01); *A61K 8/347* (2013.01); *A61K 8/365* (2013.01); *A61K 8/498* (2013.01); *A61K 8/731* (2013.01); *A61K 2800/30* (2013.01); *A61K 2800/48* (2013.01); *A61K 2800/522* (2013.01); *A61Q 17/00* (2013.01); *A61Q 19/00* (2013.01)

(58) Field of Classification Search
CPC ........ A61K 8/602; A61K 8/347; A61K 8/365; A61K 8/498; A61K 8/731; A61K 2800/30; A61K 2800/48; A61K 2800/522; A61K 8/36; A61K 2800/52; A61Q 17/00; A61Q 19/00

See application file for complete search history.

(56) References Cited

U.S. PATENT DOCUMENTS

| | | | |
|---|---|---|---|
| 4,459,285 A | 7/1984 | Grollier et al. | |
| 5,540,934 A * | 7/1996 | Touitou | A61K 8/14 424/401 |
| 10,149,808 B2 | 12/2018 | Pan et al. | |
| 10,456,343 B2 | 10/2019 | Pan et al. | |
| 10,695,278 B2 | 6/2020 | Pan et al. | |
| 10,913,870 B2 | 2/2021 | Tremitiere et al. | |
| 2017/0281503 A1* | 10/2017 | Pan | A61K 8/9789 |
| 2017/0281504 A1* | 10/2017 | Pan | A61K 8/368 |
| 2017/0281505 A1 | 10/2017 | Pan et al. | |
| 2018/0207077 A1 | 7/2018 | Pan et al. | |

FOREIGN PATENT DOCUMENTS

| | | |
|---|---|---|
| CN | 102205024 A | 10/2011 |
| CN | 105169339 A | 12/2015 |
| CN | 105997633 A | 10/2016 |
| CN | 107389830 A | 11/2017 |
| CN | 109464505 A | 3/2019 |
| JP | 2013216650 A | 10/2013 |
| JP | 2013241399 A | 12/2013 |
| JP | 2016183142 A | 10/2016 |
| KR | 20110068258 A | 6/2011 |

OTHER PUBLICATIONS

Lautenschlager (Kosmetische Praxis 2009; (4):12-15). (Year: 2009).*
Tanaka et al. (English translation of: JP2012171906) 2012; 14 pages. (Year: 2012).*
Mintel, "Crazy Cream—Tinted UV-Defense Cream," XP55701125, database accession No. 2318038, Mar. 2014, www.gnpd.com.
Search Report issued to Chinese counterpart Application No. 2020800183612 dated Nov. 17, 2022.
PCT Notification of Transmittal of the International Search Report and the Written Opinion of the International Searching Authority, issued to Application No. PCTUS2020/029272 on Jul. 1, 2020.
Marta-N Fanzone et al. "Impact of phenolic and polysaccharidic composition on commercial value of Argentinean Malbec and Cabernet Sauvignon wines" Food Research International, Amsterdam, Netherlands, Nov. 3, 2011, vol. 45 No. 1, pp. 402-414.
Wang et al. "An LC-MS method for analyzing total resveratrol in grape juice, cranberry juice, and wine", Medicinal & Aromatic PLants Abstracts, Scientific Publishers, New Delhi, India, Oct. 1, 2002, vol. 24 No. 5.
Sanchez-Gomez et al. "A potential use of vine-shoot wastes: The antioxidant, antifeedant and phytotoxic activities of their aqueous extracts", Industrial Crops and Products, Elsevier, Netherlands, Dec. 16, 2016, vol. 97 No. 16, pp. 120-127.
Mintel: Frostine's Ice on eyes Eye Gel; www.gnpd.com.
Mintel: Details of Research; www.gnpd.com.

* cited by examiner

*Primary Examiner* — Ernst V Arnold
(74) *Attorney, Agent, or Firm* — McNees Wallace & Nurick LLC

(57) ABSTRACT

A composition includes polydatin and at least one photoisomerization stabilizer and cosmetically acceptable carrier. The at least one photoisomerization stabilizer confers photostabilization to trans-polydatin by at least about 5%, relative to an otherwise identical composition without the at least one photoisomerization stabilizer.

19 Claims, No Drawings

PHOTOSTABLE ANTIOXIDANT COSMETIC COMPOSITION

CROSS-REFERENCE TO RELATED APPLICATIONS

This application is a divisional of and claims the benefit of co-pending U.S. Non-Provisional Utility application Ser. No. 16/399,313, filed on Apr. 30, 2019, and entitled "Photostable Antioxidant Cosmetic Composition," the disclosure of which is hereby incorporated by reference in its entirety.

FIELD

The present disclosure is directed to skin care compositions that include antioxidants. In particular, the compositions include polydatin and stabilizers which prevent photoisomerization of polydatin from trans- to cis- in order to preserve the benefits of polydatin to keratinous tissues, for example skin.

BACKGROUND OF THE INVENTION

The formation of free radicals is widely considered to play a significant role in the mechanisms of skin aging. Free radicals are highly reactive molecular species with unpaired electrons that can directly damage various cellular membranes, lipids, proteins, RNA and DNA. The damaging effects of said free radicals, often present in the form of reactive oxygen species, are induced inside the tissue and cells during normal metabolism and externally through various oxidative stresses. UV exposure and environmental pollution can accelerate skin aging by producing free radicals in skin. Antioxidants protect cells from the damage of oxidative stress by scavenging free radicals and inhibiting oxidation reactions. The topical application of antioxidants is broadly used in skin care products to prevent skin aging. It has been previously shown in the cosmetic related fields that polyphenols act synergistically with other antioxidants such as Vitamin E and carotenoids.

While there are some examples of antioxidants that can provide protective benefits, there remains a need for compositions which offer better options for enhancing protective formulations, particularly in the cosmetics arts.

BRIEF SUMMARY

In a first embodiment, the disclosure provides a composition that includes polydatin (also known as piceid), at least one photoisomerization stabilizer, and a cosmetically-acceptable carrier. The at least one photoisomerization stabilizer (also known as a photostabilizer) confers photo-stabilization to the polydatin by at least about 5%, relative to an otherwise identical composition without the at least one isomerization stabilizer. In some representative embodiments, the polydatin is present from about 0.05% to about 5.00% and the photoisomerization stabilizer is present from about 0.1 to about 2.5% by weight, each based on the weight of the total composition. In some embodiments, the at least one photoisomerization stabilizer confers photostabilization to the polydatin from about at least 5% to about 90%, relative to an otherwise identical composition without the at least one photoisomerization stabilizer. In some particular embodiments, the photoisomerization stabilizer includes one or more ingredients selected from sodium tetracarboxymethylchalcone, Glycosyl Hesperidin, Hesperetin, Hesperidine, Silymarin, Taxifolin, Apigenin, Baicalein, Baicalin, Luteolin, Quercetin, Hydroxycinnamate, Ferulic acid, Oryzanol, p-coumaric acid, and Mangiferin.

In some embodiments, the photoisomerization stabilizer includes at least one polyphenol, present in the composition from about 0.2% to about 5% by weight based on the weight of the composition. In some particular embodiments, the isomerization stabilizer includes at least two polyphenols, each present in the composition from about 0.1% to about 2.5% by weight based on the weight of the composition. The isomerization stabilizer may include a polyphenol that includes one or a combination of a flavanone, a flavanonol, a flavone, a hydroxycinnamate, and a xanthonoid. It will be appreciated that in some embodiments, the photostabilizer and the polydatin are present in the composition in approximately equivalent molar amounts. Thus, while some embodiments include the two components present in approximately equal amounts by weight based on the weight of the composition, there are some embodiments wherein based on differences in molecular weight, the components may be present based on weight in amounts that are not equal. In particular, in some embodiments, the polydatin is present in a composition with the at photostabilizer in amounts wherein the photostabilizer is present at or below 1 molar equivalent relative to the polydatin. Accordingly, in some embodiments, the photostabilizer may be present in a range that is from less than about 0.1% to more than about 2.5% wherein the photostabilizer is present at or below 1 molar equivalent relative to the polydatin.

In some embodiments, the composition includes a cosmetically acceptable carrier that includes one or a combination of: water present from about 45% to about 55%, one or more alcohol present from about 35% to about 40%, and one or more glycol present from about 0.5% to about 10%, or from about 1% to about 20%, each present by weight based on the weight of the composition.

In some embodiments, the composition also includes one or more additives, which in some embodiments includes at least one thickener that includes one or a combination of natural and synthetic polymers.

In some embodiments, the composition is monophasic and essentially free of oil. In other embodiments the composition is biphasic and essentially free of oil, and includes water, at least one alcohol and at least one glycol.

In a further embodiment, the disclosure provides a photo-stabilized composition that includes polydatin present from about 0.05% to about 5.00% by weight based on the weight of the composition, and an isomerization stabilizer that includes one or a mixture of polyphenols. The polyphenols are selected from caffeic acid present from about 0.2%, luteolin present from about 0.2%, hesperidine present from about 0.4%, sodium tetracarboxymethylchalcone present from about 0.4%, mangiferin present from about 0.25%, and ferulic acid present from about 0.2%. The composition also includes a cosmetically acceptable carrier. The isomerization stabilizer confers radiation stabilization to the polydatin by at least 5%, relative to an otherwise identical composition without the at least one isomerization stabilizer.

In some specific embodiments, the isomerization stabilizer includes two or more polyphenols in combinations selected from luteolin present from about 0.2% by weight, hesperidine present from about 0.4% by weight, and sodium tetracarboxymethylchalcone present from about 0.4% by weight; luteolin present from about 0.2% by weight, mangiferin present from about 0.25% by weight, and ferulic acid present from about 0.2% by weight, each based on the weight of the composition; luteolin present from about 0.2% by weight, and mangiferin present from about 0.25% by weight, each based on the weight of the composition; sodium tetracarboxymethylchalcone present from about 0.4% by weight, and ferulic acid present from about 0.2% by weight, each based on the weight of the composition; luteolin present from about 0.2% by weight, and ferulic acid present from about 0.2% by weight, each based on the weight of the composition; caffeic acid present from about 0.2% by weight, luteolin present from about 0.2% by weight, and mangiferin present from about 0.25% by weight, each based on the weight of the composition, and caffeic acid present from about 0.2% by weight, and ferulic acid present from about 0.2% by weight, each based on the weight of the composition. According to some such embodiments, the cosmetically acceptable carrier in the composition includes one or a combination of water present from about 45% to about 55%, an alcohol present from about 35% to about 40%, and a glycol present from about 0.5% to about 3.0%, or up to about 20%, each present by weight based on the weight of the composition.

These and other aspects of the invention are set out in the appended claims and described in the detailed description of the invention.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

It is to be understood that both the foregoing general description and the following detailed description are exemplary and explanatory only and are not restrictive of the disclosure.

DETAILED DESCRIPTION

In the present application, the terms "keratinous substrate" and "keratinous tissue" each includes but is not limited to skin, hair, and nails.

"Cosmetically acceptable" means a carrier that is compatible with any keratinous substrate.

As used herein, "serum" refers to a hydrophilic liquid composition formulated for topical application. A serum may optionally be free from or essentially free from one or more of an oil, including an emollient, a wax and a silicone oil.

The disclosure provides compositions that include polydatin. In some embodiments, the compositions are photo-stable serums containing polydatin. The compositions may be monophasic or biphasic, according to the described embodiments.

Polydatin (3,4',5-trihydroxystibene-3-β-mono-D glucoside) and its derivatives are stilbenoids with known strong natural antioxidant properties of free-radical quenching and limitation of oxidative stress. These properties can be used for a skincare or suncare product, including compositions according to the disclosure. When exposed to sun light, polydatin, which is active in a trans-conformation, isomerizes into cis-polydatin.

The below formulae (I) demonstrate the structural change in polydatin upon radiation induced isomerization from trans- to cis-.

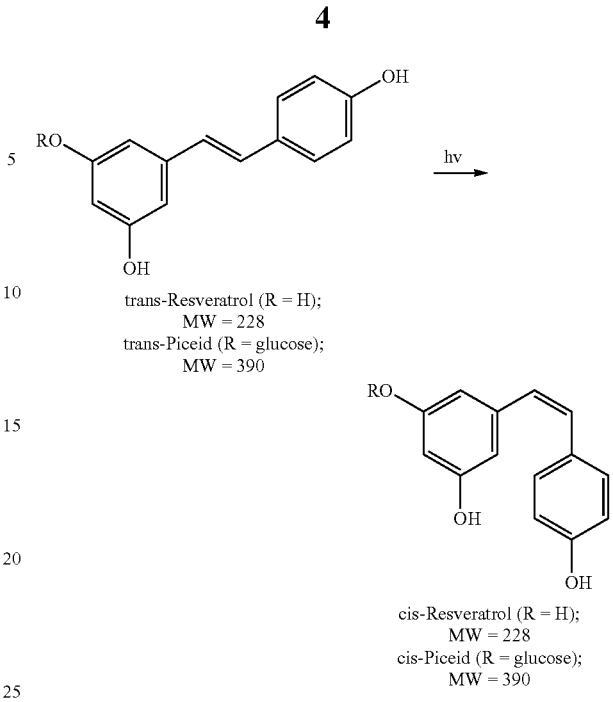

trans-Resveratrol (R = H);
MW = 228
trans-Piceid (R = glucose);
MW = 390 cis-Resveratrol (R = H);
MW = 228
cis-Piceid (R = glucose);
MW = 390

The photo-instability of polydatin has limited its use in cosmetic products. Provided herein are inventive compositions in the context of a cosmetically acceptable carrier wherein polydatin is formulated to be stabilized by inclusion of one or more photoisomerization stabilizers. These photoisomerization stabilizers include, in some embodiments, polyphenols. As further described herein and as exemplified in the non-limiting examples, the photoisomerization stabilizers may be selected from one or more, and in some examples, from a combination of at least two polyphenols. For example, the compositions may include two or more of the nonlimiting examples of photoisomerization stabilizers comprising polyphenols selected from sodium tetracarboxymethylchalcone, caffeic acid, luteolin, mangiferin, hesperidine, and ferulic acid.

The disclosure demonstrates that the inventive compositions provide altered and enhanced photostability of polydatin. As further exemplified herein, samples of trans-polydatin (in non-limiting exemplified compositions present at about 0.50%) was formulated in a serum with one or more photoisomerization stabilizers. After irradiation of each sample at 365 nm with 5 J/cm$^2$ energy, the amount of residual trans-polydatin was measured using HPLC-UV, wherein the residual amount of trans-polydatin is represented by the ratio between the final (post irradiation) and the initial (pre-irradiation) concentration of trans-polydatin as measured by HPLC-UV. The compositions formulated according to the disclosure provide a high degree of retention of trans-polydatin activity as compared to compositions that lack the one or more photoisomerization stabilizers.

Provided in various embodiments are compositions that include polydatin, at least one photoisomerization stabilizer, and a cosmetically acceptable carrier. The at least one photoisomerization stabilizer confers photostabilization to the polydatin (to protect the trans-form from photoisomerization) from about at least about 5% to about 90%, relative to an otherwise identical composition without the at least one photoisomerization stabilizer. In some embodiments, the photostabilization conferred as reflected in the concentration of trans-polydatin is from about at least 5% to about 90%, or in some embodiments in solution from about 10% to upwards of 95%. Thus, the photostabilization may be from at least 5% or from about 10%, to about 85%, or to about 90%, or to about 95% or more, including 5, 6, 7, 8, 9, 10, 15, 20, 25, 30, 35, 40, 45, 50, 55, 60, 65, 70, 75, 80, 85, 90, 95 to more than 95%.

In some particular embodiments, the photoisomerization stabilizer includes a combination of at least two photoisomerization stabilizers selected from sodium tetracarboxymethylchalcone, glycosyl hesperidin, hesperetin, hesperidine, silymarin, taxifolin, apigenin, baicalein, baicalin, luteolin, quercetin, hydroxycinnamate, ferulic acid, oryzanol, p-coumaric acid, and mangiferin.

Polydatin

In accordance with the various embodiments, polydatin is present in the compositions according to the disclosure. As previously mentioned, polydatin, which may be described by the following, 3,4',5-trihydroxystibene-3-β-mono-D glucoside, and which is also known as piceid, along with its derivatives, is a stilbenoid. Stilbenoids have strong natural antioxidant properties of free-radical quenching and limitation of oxidative stress. These properties can be used for a skincare or suncare products, including compositions according to the disclosure. When exposed to sun light or other radiation, polydatin, which is active in a trans-conformation, photoisomerizes into cis-polydatin which has less biological activity.

Polydatin may be obtained in raw material reagents that contain amounts from less than 50% and up to 99% or greater. Some isolates and extracts can be obtained that contain polydatin which is pure or essentially pure.

In accordance with the various embodiments, polydatin active is present in the composition from about 0.05% to about 5.0%, or from about 0.1% to about 4.0%, or from about 0.2% to about 3.0%, or from about 0.4% to about 2.0%, or from about 0.5% to about 1.0% or any suitable combination, sub-combination, range, or sub-range thereof by weight, based on the weight of the composition. One of ordinary skill in the art, however, will appreciate that other ranges are within the scope of the invention.

Thus, polydatin in the composition is present by weight, based on the total weight of the composition, from about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5 to about 5.0 percent, including increments and ranges therein and there between.

Photoisomerization Stabilizers

In accordance with the various embodiments, one or more photoisomerization stabilizers are present in the compositions according to the disclosure. A photoisomerization stabilizer is present from about 0.1% to about 2.0% by weight, based on the weight of the composition. A combination of photoisomerization stabilizers may be present from a total amount that includes about 0.1% to about 4.0% by weight, of each isomerization stabilizer, based on the weight of the composition.

Polyphenols

In accordance with some embodiments, the photoisomerization stabilizers include one more polyphenols. Phenolic compounds are a structural class of natural, synthetic, and semisynthetic organic compounds that have one or more phenolic constituents. Phenolic compounds containing multiple phenol groups are known as polyphenols. Polyphenols are normally available in plants and are very helpful to protect plants and also animals from usual health disorders and also the impacts of aging. Polyphenols function as potent free radical scavengers by donating their alcoholic hydrogen or one of their delocalized electrons. The two classes of polyphenols are flavonoids and non-flavonoids.

Flavonoids are a specific group of polyphenols, and are the most plentiful group of polyphenol compounds, making up about two-thirds of the total phenols in consumed feed. Flavonoids are further categorized, according to chemical structure, into chalcones, flavones, flavanones, flavanols, dihydroflavonols, isoflavonoids, neoflavonoids, catechins, anthocyanidins, and tannins. Over 4,000 flavonoids have been identified, many of which occur in fruits, vegetables and beverages (tea, coffee, beer, wine and fruit drinks). The flavonoids have been reported to have antiviral, anti-allergic, antiplatelet, anti-inflammatory, antitumor and antioxidant activities. Flavonoids protect lipids and vital cell components from damaging oxidative stress by efficiently scavenging free radicals.

In some particular embodiments, the photoisomerization stabilizer includes one or a combination of sodium tetracarboxymethylchalcone, glycosyl hesperidin, hesperetin, hesperidine, silymarin, taxifolin, apigenin, baicalein, baicalin, luteolin, quercetin, hydroxycinnamate, ferulic acid, oryzanol, p-coumaric acid, and mangiferin. The aforementioned specific examples of photoisomerization stabilizers include naturally derived extracts or isolates. The polyphenols may be obtained in raw material reagents that contain amounts from less than 70% and up to 99% or greater of the identified polyphenols. Some isolates and extracts can be obtained that contain a polyphenol up to 100% in purity. Thus, it will be appreciated that raw materials that may be selected as "an isolate or extract comprising a specific polyphenol up to 100% in purity" means and includes but is not limited to an extract comprising one or more of a specifically identified polyphenol, including the polyphenols used in the exemplified embodiments herein.

Except as may be expressly provided herein, the raw material forms that include any exemplified polyphenol are provided at a concentration of from less than to up to 100% active. Thus, extracts may include less than 100% of the polyphenol active; otherwise, an exemplified composition includes raw materials included by weight in a composition based on an original concentration of active which is pure or essentially pure.

In accordance with the various embodiments, a photoisomerization stabilizer, selected in some embodiments from polyphenols, is present in the composition from about 0.1% to about 2.5%, or from about 0.15% to about 1.5%, or from about 0.2% to about 1.0%, or from about 0.25% to about 0.5%, or from about 0.3% to about 0.4% or any suitable combination, sub-combination, range, or sub-range thereof by weight, based on the weight of the composition. One of ordinary skill in the art, however, will appreciate that other ranges are within the scope of the invention.

As mentioned herein above, in some particular embodiments, the photostabilizer includes at least two polyphenols, each present in the composition from about 0.1% to about 2.5% by weight based on the weight of the composition. Thus, it will be appreciated that in some embodiments, the photostabilizer and the polydatin are present in the composition in approximately equivalent molar amounts. Thus, while some embodiments include the two components present in approximately equal amounts by weight based on the weight of the composition, there are some embodiments wherein based on differences in molecular weight, the components may be present based on weight in amounts that are not equal. In particular, in some embodiments, the polydatin is present in a composition with the at photostabilizer in amounts wherein the photostabilizer is present at or below 1 molar equivalent relative to the polydatin. Accordingly, in some embodiments, the photostabilizer may be present in a range that is from less than about 0.1% to more than about 2.5% wherein the photostabilizer is present at or below 1 molar equivalent relative to the polydatin.

Thus, one or more photoisomerization stabilizers in the composition is present by weight, based on the total weight of the composition, from about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, to about 2.0 percent, including increments and ranges therein and there between.

Further, in some specific embodiments, any one of the specific exemplified polyphenols, such as sodium tetracarboxymethylchalcone, glycosyl hesperidin, hesperetin, hesperidine, silymarin, taxifolin, apigenin, baicalein, baicalin, luteolin, quercetin, hydroxycinnamate, ferulic acid, oryzanol, p-coumaric acid, and mangiferin, may be present in an composition according to the disclosure in a weight percent amount that is determined as the product of the percentage purity of the antioxidant in the extract and the percentage of the extract used in the formulation, for example, from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, to about 20 percent by weight, including increments and ranges therein and there between.

In certain embodiments, one or more of caffeic acid is present from about 0.2% up to about 2%, luteolin present from about 0.2% up to about 2%, hesperidine present from about 0.4% up to about 2%, sodium tetracarboxymethylchalcone present from about 0.4% up to about 2%, mangiferin present from about 0.25% up to about 2%, and ferulic acid present from about 0.2%.

Optional Additional Antioxidants

In accordance with the various embodiments, compositions may contain one or more additional antioxidants that is/are different from the polyphenols used in the composition. Additional antioxidants can be any antioxidant suitable for use in cosmetic formulations. Suitable antioxidants include, but are not limited to, amino acids and derivatives thereof, imidazoles, peptides such as carnosine and derivatives, carotenoids, carotenes (such as α-carotene, β-carotene, and lycopene), α-hydroxy acids (such as citric acid, lactic acid, or malic acid), tocopherols and derivatives (such as Vitamin E), vitamin A, co-enzyme Q10, bioflavonoids, glutathione, plant extracts (such as rosemary extract, olive leaf extracts), and green tea extracts, lignans, and aurones.

The amount of additional antioxidants, if any, present in the compositions can range from about 0.01% to about 20%, or from about 0.1% to about 20%, or from about 0.01% to about 2%, based on the total weight of the composition.

Cosmetically Acceptable Carrier

In accordance with the various embodiments, the compositions include a cosmetically acceptable carrier. The total amount of the cosmetically acceptable carrier in compositions may be from about 40% to about 99%, based on the total weight of the composition.

The cosmetically acceptable carrier can include, for example, water and organic solvents such as glycerin, C1-4 mono-alcohols, polyols, glycols, and combinations thereof. As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

In some embodiments, the cosmetically acceptable carrier includes water and one or more water soluble components, for example, glycerin, C1-4 alcohols, polyols, glycols, and combinations thereof. In some embodiments, the cosmetically acceptable carrier includes water, or a mixture of water and one or more cosmetically acceptable organic solvent, or one or more cosmetically acceptable organic solvent. In a representative embodiment, a cosmetically acceptable carrier according to the disclosure includes one or a combination of: water present from about 45% to about 55%, one or more alcohol present from about 35% to about 40%, and one or more glycol present from about 0.5% to about 3.0%, each present by weight based on the weight of the composition.

In some embodiments, the cosmetically acceptable carrier may comprise one or more glycols. For example, the one or more glycols can include ethylene glycol, propylene glycol, butylene glycol, caprylyl glycol, hexylene glycol, dipropylene glycol, and diethylene glycol. The total amount of one glycol, if present, may be from about 0.1% to about 5%, or from about 0.5% to about 3% based on the total weight of the composition.

In some embodiments, the cosmetically acceptable carrier may comprise one or more alcohols. For example, the one or more alcohols can include monoalcohols and polyols such as ethyl alcohol, isopropyl alcohol, propyl alcohol, benzyl alcohol, and phenylethyl alcohol. The total amount of an alcohol, if present, may be from about 25% to 50%, from about 35% to 40%, based on the total weight of the composition.

In some specific embodiments, the cosmetically acceptable carrier may comprise one or more alcohols and one or more glycols. In one representative embodiment, the one or more alcohols can include a monoalcohol present from about 35% to about 45% and the one or more glycols includes pentylene glycol and dipropylene glycol, each present from about 0.5% to about 3.0%. In some such embodiments, the cosmetically acceptable carrier also includes water present from about 45% to about 55%.

Further, in the various embodiments, the composition may include one or more glycol, for example, glycerin, present in the composition in the range from about 0.5% to about 25% by weight, or from about 1% to about 20%, or from about 5% to about 15%, or from about 3% to about 10%, or from about 3% to about 8% by weight based on the total weight of the composition.

In some embodiments, the total amount of water in the composition is from about 20% to about 99%, or from about from about 30% to about 80%, or from about 40% to about 75%, or from about 45% to about 60% based on the total weight of the composition.

Thus, a cosmetically acceptable carrier includes one or more components, in some embodiments selected from water, organic solvents including alcohols, and glycols in the composition is present by weight, based on the total weight of the composition, within the specific ranges as described above, from about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 3, 4, 5, 6, 7, 8, 9 10, 11, 12, 13, 14, 15, 16, 17, 18, 19, 20, 25, 30, 35, 40, 45, 50, 55, 60, 65, 70, 75, 80, 85, 90, 95 to about 99 percent, including increments and ranges therein and there between.

The pH of the compositions is not limited but is generally between 2 and 12, or between 3 and 9. The pH can be adjusted to the desired value by addition of a base (organic or inorganic) to the composition, for example ammonia or a primary, secondary or tertiary (poly)amine, such as monoethanolamine, diethanolamine, triethanolamine, isopropanolamine or 1,3-propanediamine, or alternatively by addition of an inorganic or organic acid, advantageously a carboxylic acid, such as, for example, citric acid.

In some embodiments, the compositions may not have a pH which is measurable.

Optional Thickeners

In accordance with some embodiments, the compositions may include a thickener. The total amount of a thickener that may be present in a composition is from about 0.1% to about 5% by weight based on the total weight of the composition.

In some embodiments the compositions include at least one thickener that includes one or a combination of natural and synthetic polymers. In some specific embodiments, the thickener may comprise one or more thickeners selected among associative acrylate-based thickeners, taurate-based thickeners, waxes, gums, cellulose derivatives, and other polysaccharides.

In some embodiments, the total amount of thickener in the composition is from about 0.1% to about 5%, or from about 0.2% to about 4%, or from about 0.3% to about 3%, or from about 0.4% to about 3%, or from about 0.5% to about 2%, or from about 0.6% to about 1% based on the total weight of the composition.

Thus, a thickener, if present in the composition is present by weight, based on the total weight of the composition, from about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5 to about 5.0 percent, including increments and ranges therein and there between.

In some particular embodiments, the compositions include one or more thickeners that include hydroxypropyl methylcellulose, present from about 0.5% by weight based on the weight of the composition.

Optional Additives

The compositions can also comprise at least one additive used in the cosmetics field which does not affect the properties of the compositions according to the invention, such as thickeners, fragrances, pearlescent agents, preservatives, sunscreens, anionic or nonionic or cationic or amphoteric polymers, proteins, protein hydrolysates, vitamins, panthenol, silicones, gelling agents, odor absorbers, and colorants. Additives used according to the disclosure may be selected from actives, including but not limited to: anti-microbial components, including, but not limited to, caproyl glycine and sodium salicylate; essential oils selected from the group consisting of sunflower oil, sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, and ylang ylang; fruit extracts, for example *Pyrus malus* (Apple) Fruit Extract, and Aloe Barbadensis Leaf Juice Powder; citric acid, sodium chloride; acetyl trifluoromethylphenyl valylglycine and combinations thereof. Although the optional active additives are given as examples, it will be appreciated that other optional components compatible with cosmetic applications known in the art may be used.

Also, in accordance with the disclosure, in some embodiments, there may be one or more other cosmetically acceptable additives present in the cosmetic composition. In some embodiments, cosmetically acceptable additives used according to the disclosure may be selected from colorants, preservatives, fragrances, dyes, neutralizing or pH-adjusting agents (e.g., triethylamine (TEA), sodium hydroxide, citric acid, and hydrochloric acid). Although the optional additives are given as examples, it will be appreciated that other optional components compatible with cosmetic applications known in the art may be used.

In some particular embodiments, the composition includes one or a combination of actives and additives selected from sodium chloride and panthenol.

In accordance with the various embodiments, the amount of one or more actives and additives, alone or in combination, present in the composition can be present in the composition according to the disclosure in a range from about 0.001% to about 20%, by weight, or from about 0.005% to about 0.01%, or from about 0.01% to about 0.1%, or from about 0.15% to about 5%, or from about 0.40% to about 4%, or from about 0.5% to about 2% by weight, or from about 1% to about 2%, or any suitable combination, sub-combination, range, or sub-range thereof by weight, based on the total weight of the composition.

Thus, any one or a combination of actives and additives may be present, by weight, based on the total weight of the composition, each one or the combination present from about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 weight percent, including increments and ranges therein and there between.

Formulations Comprising the Compositions

Generally, any composition of the invention can be applied to a keratinous substrate or tissue. For topical application to the skin, the composition can have the form in particular of aqueous mono or biphasic water-based formulations.

EXAMPLES

Example 1

TABLE 1

| | Inventive Compositions | | | | |
|---|---|---|---|---|---|
| Ingredient | Inventive 1 | Inventive 7 | Inventive 8 | Inventive 9 | Inventive 10 |
| Caffeine | 1 | 1 | 1 | 1 | 1 |
| Ferulic Acid | | | 0.2 | | 0.2 |
| *Mangifera Indica* (Mango) Leaf Extract | | | 0.25 | 0.25 | |
| Polygonum Cuspidatum Root Extract | 0.5 | 0.5 | 0.5 | 0.5 | 0.5 |
| Hesperidin | | 0.4 | | | |

TABLE 1-continued

Inventive Compositions

| Ingredient | Inventive 1 | Inventive 7 | Inventive 8 | Inventive 9 | Inventive 10 |
|---|---|---|---|---|---|
| Caffeic Acid | 0.2 | | | | |
| Sodium Tetracarboxymethyl chalcone | | 0.4 | | | 0.4 |
| Chrysanthemum Morifolium Leaf Extract | 0.2 | 0.2 | 0.2 | | |
| Hydroxypropyl Methylcellulose | 0.5 | 0.5 | 0.5 | 0.5 | 0.5 |
| Dipropylene Glycol | 2.5 | 2.5 | 2.5 | 2.5 | 2.5 |
| Alcohol Denat. | 39.2 | 39.2 | 39.2 | 39.2 | 39.2 |
| Pentylene Glycol | 2.5 | 2.5 | 2.5 | 2.5 | 2.5 |
| Panthenol | 1 | 1 | 1 | 1 | 1 |
| Citric Acid | | | | | |
| Water | 52.6 | 51.8 | 52.2 | 52.4 | 52.2 |

Referring to Table 1, above, each of the inventive compositions are provided in a cosmetically acceptable carrier according to the disclosure, and numbers indicate proportion of ingredients by weight percent. Other inventive examples as presented in the further examples below were formulated in a cosmetically acceptable carrier that includes the alcohol, glycol, and water solvents that are the same or comparable to those listed above in the general amounts as shown, including such other optional additives as may be listed above or mentioned in the description.

Example 2: Evaluation of Polydatin Stabilization/Photoprotection with Various Polyphenolic Isomerization Stabilizers The stabilization of polydatin was evaluated in a solution-based assay where residual trans-polydatin percentage was determined after exposure to radiation. According to the experimental method, trans-polydatin was dissolved in an appropriate solvent at 0.5% by weight. To this solution was added 1 molar equivalent of an isomerization stabilizer. An aliquot of the resulting solution was diluted with methanol and the amount of trans-polydatin was quantified by HPLC-UV. The solution containing trans-polydatin and the additive was irradiated under controlled conditions at 365 nm using 5 J of total energy. An aliquot of the irradiated solution was diluted in methanol and the amount of trans-polydatin was quantified by HPLC-UV. The residual trans-polydatin was calculated by dividing the quantified amount of trans-polydatin obtained from the irradiated solution by the amount of trans-polydatin obtained from the non-irradiated solution and is expressed as a percentage. The relative residual is indicated for each photoisomerization stabilizer and is calculated as an average relative residual for classes of photoisomerization stabilizers where indicated. For example, for example, "flavonoids" are calculated as an average residual for all molecules which are flavonoids, whereas "hydroxycinnamates" are calculated as an average residual for all molecules which are hydroxycinnamates, etc.

TABLE 2

Average of Relative Residual Trans-polydatin after irradiation

| Photoisomerization Stabilizer (polyphenol type/polyphenol) | Average of Relative Residual Trans-polydatin (percent) |
|---|---|
| Flavonoids | 36.7 |
| Flavanols | 0.4 |
| Epigallocatechine gallate | 0.4 |
| Flavanones | 33.4 |
| Glycosyl Hesperidin | 31.0 |
| Hesperetin | 30.6 |
| Hesperidine | 41.6 |
| Flavanonols | 27.8 |
| Silymarin | 22.6 |
| Taxifolin | 38.3 |
| Flavones | 54.4 |
| Apigenin | 66.7 |
| Baicalein | 42.9 |
| Baicalin | 32.3 |
| Luteolin | 63.3 |
| Flavonols | 24.8 |
| Quercetin | 24.8 |
| Hydroxycinnamates | 43.8 |
| Ferulic acid | 35.5 |
| Oryzanol | 57.2 |
| p-coumaric acid | 38.6 |
| Others | 0.5 |
| BHT | −3.1 |
| Gallic acid | −0.3 |
| Mandelic acid | −0.9 |
| Niacinamide | −0.3 |
| Vitamin CG | 6.9 |
| Vitamin E | 0.6 |
| Xanthonoids | 44.6 |
| Mangiferin | 44.6 |

As shown in Table 2, above, flavonoids, hydroxycinnamates, and xanthonoids demonstrate significant and unexpected photo-stabilization of trans-polydatin in solution. Among flavonoids, all show an ability to improve photostability of trans-polydatin with the notable exception of flavanols. The flavanols lack a carbonyl moiety adjacent to the aromatic system. Without being bound by theory or mechanism, it is posited that this structural difference affects the functionality of these flavanols to confer stabilization of trans-polydatin. Among other common antioxidants and photostabilizers tested, notably niacinamide was found to be ineffective as a means to improve the photostability of flavanols. Equally ineffective included vitamin CG (an ascorbic acid derivative), vitamin E, mandelic acid, gallic acid, and BHT (tert-butylhydroxytoluene).

Example 3: Evaluation of Trans-Polydatin Photostabilization with and without Photoisomerization Stabilizers The photostabilization of polydatin was evaluated on a solid substrate (acrylic plate) assay where residual trans-polydatin was determined after exposure to radiation. According to the experimental method, trans-polydatin at 0.5% by weight was formulated in a serum with photoisomerization stabilizers and each formulation was applied to a plastic substrate. Each formulation was irradiated at 365 nm with 5 J/cm² energy, and then the residual trans-polydatin was measured using HPLC. The results are presented in the table below. The residual amount of trans-polydatin corresponds to the ratio between the final (post irradiation) and the initial (pre-irradiation) concentration of trans-polydatin. (Note: the relative residual trans-polydatin values as shown below are determined by a method that is different from the method of Example 2; thus, the reported amounts of trans-polydatin are specific to each experiment and are not equivalent between the two experimental methods.)

TABLE 3

Polydatin Photoisomerization Protection Study with and without photoisomerization stabilizers

| Inventive Composition | Polydatin with and without Photo-isomerization Stabilizer(s) | Residual trans-polydatin |
|---|---|---|
| Comparative Control | 0.5% polydatin | 55 |
| Inventive 1 | +0.2% caffeic acid | 86 |
| Inventive 2 | +0.2% Luteolin | 84 |
| Inventive 3 | +0.4% hesperidine | 71 |
| Inventive 4 | +0.4% TCM chalcone | 82 |
| Inventive 5 | +0.25% Mangiferin | 82 |
| Inventive 6 | +0.2% ferulic acid | 85 |
| Inventive 7 | +0.4% hesperidine +0.4% TCM Chalcone +0.2% luteolin | 89 |
| Inventive 8 | +0.2% luteolin +0.25% Mangiferin +0.2% ferulic acid | 92 |
| Inventive 9 | +0.2% luteolin +0.25% Mangiferin | 89 |
| Inventive 10 | +0.4% TCM Chalcone +0.2% ferulic acid | 87 |
| Inventive 11 | +0.2% luteolin +0.2% ferulic acid | 88 |
| Inventive 12 | +0.2% luteolin +0.25% Mangiferin +0.2% caffeic acid | 90 |
| Inventive 13 | +0.2% caffeic acid +0.2% ferulic acid | 88 |

Referring to Table 3, above, the data show that one or a mixture of the photoisomerization stabilizers in a cosmetically acceptable carrier is able to act as a photostabilizer for the trans-polydatin. As shown, when a mixture of at least 2 of these photoisomerization stabilizers is added to a composition including trans-polydatin, the residual amount of trans-polydatin after irradiation is much higher than the residual amount of trans-polydatin in the absence of any photoisomerization stabilizers.

While the disclosure has been described with reference to a preferred embodiment, it will be understood by those skilled in the art that various changes may be made, and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

The term "clear" as used herein means that after applying a film of the composition onto a glass plate, and then placing the glass plate over top of a printed document, a person is able to read 12-point font through the film+plate with their naked eye.

The articles "a" and "an," as used herein, mean one or more when applied to any feature in embodiments of the present disclosure described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"At least one," as used herein, means one or more and thus includes individual components as well as mixtures/combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed disclosure. All materials and methods described herein that embody the present disclosure can, in alternate embodiments, be more specifically defined by any of the transitional terms "comprising," "consisting essentially of," and "consisting of."

The terms "free" and "devoid" indicates that no reliably measurable excluded material is present in the composition, typically 0% by weight, based on the total weight of the composition. The term "essentially free" means that, while it prefers that no excluded material is present in the composition, it is possible to have very small amounts of the excluded material in the composition of the invention, provided that these amounts do not materially affect the advantageous properties of the composition. In particular, "essentially free" means that excluded material can be present in the composition at an amount of less than about 0.1% by weight, based on the total weight of the composition.

Other than in the operating examples, or where otherwise indicated, all numbers expressing quantities of ingredients and/or reaction conditions are to be understood as being modified in all instances by the term "about," meaning within 10% of the indicated number (e.g. "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used and may or may not reflect the final percentage of the active, wherein the final percentage of the active is dependent on the weight percent of active in the raw material.

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:

1. A composition comprising:
   i) polydatin present from about 0.05% to about 5.00% by weight based on the weight of the composition;
   ii) a combination of photoisomerization stabilizers, each photoisomerization stabilizer present from about 0.1% to about 2.5% by weight based on the weight of the composition, the combination of photoisomerization stabilizers including luteolin and mangiferin; and
   iii) a cosmetically acceptable carrier,
   wherein the at least one or combination of photoisomerization stabilizers confers photostabilization to the polydatin by at least 5%, relative to an otherwise identical composition without the at least one or combination of photoisomerization stabilizers, and
   wherein the composition is free of baicalin.

2. The composition according to claim 1, wherein the total amount of photoisomerization stabilizers present in the composition is from about 0.1% to about 2.5% by weight based on the weight of the composition.

3. The composition according to claim 1, wherein each one of the at least one or combination of photoisomerization stabilizers is present in the composition from about 0.1% to about 0.4% by weight based on the weight of the composition, and polydatin is present from about 0.4% to about 1.0%.

4. The composition according to claim 1, wherein the at least one or combination of photoisomerization stabilizers includes at least one of ferulic acid, or caffeic acid, or a combination thereof.

5. The composition according to claim 1, wherein the cosmetically acceptable carrier comprises one or a combination of: water present from about 45% to about 55%, one or more monoalcohol present from about 35% to about 40%, and one or more glycol present from about 0.5% to about 3.0%, each present by weight based on the weight of the composition.

6. The composition according to claim 5, wherein the composition includes at least one additive, wherein the at least one additive includes one or more thickeners comprising one or a combination of natural and synthetic polymers.

7. The composition according to claim 6, wherein the at least one additive includes one or more thickeners comprising hydroxypropyl methylcellulose, present from about 0.05% to about 5% by weight based on the weight of the composition.

8. The composition according to claim 1, wherein the composition is monophasic and contains oil at an amount of less than 0.1% by weight, based on the total weight of the composition.

9. The composition according to claim 1, wherein the at least one or combination of photoisomerization stabilizers confers photostabilization to the polydatin from about at least 5% to about 90%, relative to an otherwise identical composition without the at least one or combination of photoisomerization stabilizers.

10. A composition comprising:
    i) polydatin present from about 0.05% to about 5.00% by weight based on the weight of the composition;
    ii) at least one photoisomerization stabilizer present in the composition from about 0.1% to about 2.5% by weight based on the weight of the composition, the at least one photoisomerization stabilizer selected from the group consisting of:
       (1) a combination of mangiferin and caffeic acid;
       (2) a combination of luteolin and mangiferin;
       (3) a combination of luteolin, mangiferin, and ferulic acid;
       (4) a combination of luteolin, mangiferin, and caffeic acid;
       (5) a combination of caffeic acid and ferulic acid;
       (6) a combination of hesperidine, sodium tetracarboxymethylchalcone, and luteolin;
       (7) apigenin;
       (8) baicalein;
       (9) luteolin;
       (10) oryzanol;
       (11) a combination of mangiferin, ferulic acid, and caffeic acid; and
       (12) combinations thereof; and
    iii) a cosmetically acceptable carrier that includes one or a combination of water, at least one monoalcohol, and at least one glycol,
    wherein the at least one photoisomerization stabilizer confers photostabilization to the polydatin by at least 5%, relative to an otherwise identical composition without the at least one photoisomerization stabilizer, and
    wherein the composition is free of baicalin.

11. The composition according to claim 10, wherein each one of the at least one or combination of photoisomerization stabilizers is present in the composition from about 0.2% to about 0.4% by weight based on the weight of the composition and polydatin is present from about 0.4% to about 2.0% by weight based on the weight of the composition.

12. The composition according to claim 10, wherein polydatin is present from about 0.4% to about 1.0% by weight, based on the total weight of the composition.

13. The composition according to claim 10, wherein, when present,
    luteolin is present from about 0.2% by weight based on the weight of the composition;
    mangiferin is present from about 0.25% by weight based on the weight of the composition;
    ferulic acid is present from about 0.2% by weight based on the weight of the composition;
    caffeic acid is present from about 2% by weight based on the weight of the composition;

hesperidine is present from about 0.4% by weight based on the weight of the composition; and sodium tetracarboxymethylchalcone is present from about 0.4% by weight based on the weight of the composition.

14. The photo-stabilized composition according to claim 10, wherein water is present from about 45% to about 55%, at least one monoalcohol is present from about 35% to about 40%, and at least one glycol is present from about 0.5% to about 3.0%, each present by weight based on the weight of the composition.

15. The composition according to claim 10, wherein the composition includes at least one additive that includes one or more thickeners comprising hydroxypropyl methylcellulose, present from about 0.05% to about 5% by weight based on the weight of the composition.

16. The composition according to claim 10, wherein the composition is a biphasic composition.

17. The composition according to claim 10, wherein the at least one photoisomerization stabilizer is selected from the group consisting of:
   (1) a combination of luteolin present at 0.2% and mangiferin present at 0.25%;
   (2) a combination of luteolin present at 0.2%, mangiferin present at 0.25%, and ferulic acid present at 0.2%;
   (3) a combination of luteolin present at 0.2%, mangiferin present at 0.25%, and caffeic acid present at 0.2%;
   (4) a combination of hesperidine present at 0.4%, sodium tetracarboxymethylchalcone present at 0.4%, and luteolin present at 0.2%; and
   (5) a combination of caffeic acid present at 0.2% and ferulic acid present at 0.2%, all amounts by weight based on the weight of the composition.

18. A composition comprising:
   i) polydatin present at about 0.5% by weight based on the weight of the composition;
   ii) a combination of photoisomerization stabilizers, the combination selected from the group consisting of
      (1) luteolin present at 0.2% and mangiferin present at 0.25%;
      (2) luteolin present at 0.2%, mangiferin present at 0.25% and ferulic acid present at 0.2%;
      (3) luteolin present at 0.2%, mangiferin present at 0.25%, and caffeic acid present at 0.2%;
      (4) hesperidine present at 0.4%, sodium tetracarboxymethylchalcone present at 0.4%, and luteolin present at 0.2%; and
      (5) caffeic acid present at 0.2% and ferulic acid present at 0.2%; and
   iii) a cosmetically acceptable carrier,
   wherein the composition is free of baicalin.

19. The photo-stabilized composition according to claim 18, wherein water is present from about 45% to about 55%, at least one of monoalcohol is present from about 35% to about 40%, and at least one glycol is present from about 0.5% to about 3.0%, each present by weight based on the weight of the composition.

* * * * *